(12) United States Patent
Missbichler

(10) Patent No.: US 10,898,464 B2
(45) Date of Patent: *Jan. 26, 2021

(54) TANNIN AND ANTI-GLIADIN ANTIBODY COMPOSITIONS FOR TREATMENT OF A DISEASE OF THE INTESTINAL TRACT

(71) Applicant: STADA ARZNEIMITTEL AG, Bad Vilbel (DE)

(72) Inventor: Albert Missbichler, Vienna (AT)

(73) Assignee: STADA ARZNEIMITTEL AG, Bad Vilbel (DE)

( * ) Notice: Subject to any disclaimer, the term of this patent is extended or adjusted under 35 U.S.C. 154(b) by 400 days.

This patent is subject to a terminal disclaimer.

(21) Appl. No.: 15/638,638

(22) Filed: Jun. 30, 2017

(65) Prior Publication Data

US 2017/0304259 A1    Oct. 26, 2017

Related U.S. Application Data

(63) Continuation of application No. 14/367,171, filed as application No. PCT/AT2012/050200 on Dec. 19, 2012, now Pat. No. 9,724,326.

(30) Foreign Application Priority Data

Dec. 19, 2011    (AT) .............................. A 50010/2011

(51) Int. Cl.
| | | |
|---|---|---|
| A61K 31/353 | (2006.01) | |
| A61K 39/395 | (2006.01) | |
| A61K 35/74 | (2015.01) | |
| A61K 35/745 | (2015.01) | |
| A61K 35/747 | (2015.01) | |
| A61K 36/062 | (2006.01) | |
| A61K 35/00 | (2006.01) | |
| A61K 39/00 | (2006.01) | |

(52) U.S. Cl.
CPC ............ *A61K 31/353* (2013.01); *A61K 35/74* (2013.01); *A61K 35/745* (2013.01); *A61K 35/747* (2013.01); *A61K 36/062* (2013.01); *A61K 39/395* (2013.01); *A61K 39/39583* (2013.01); *A61K 2035/115* (2013.01); *A61K 2039/505* (2013.01); *A61K 2039/51* (2013.01); *A61K 2039/52* (2013.01); *A61K 2039/55511* (2013.01)

(58) Field of Classification Search
None
See application file for complete search history.

(56) References Cited

U.S. PATENT DOCUMENTS

| | | | |
|---|---|---|---|
| 9,724,326 B2* | 8/2017 | Missbichler | A61K 39/395 |
| 2003/0143292 A1* | 7/2003 | Cho | A61K 36/82 |
| | | | 424/756 |
| 2003/0143293 A1 | 7/2003 | Shushunov | 424/773 |
| 2010/0129418 A1 | 5/2010 | Lawrence et al. | 424/423 |
| 2011/0008362 A1 | 1/2011 | Sunwoo et al. | 424/157.1 |

FOREIGN PATENT DOCUMENTS

WO    WO 2008/119012    10/2008

OTHER PUBLICATIONS

"Tannacomp," Medice, Mar. 1, 2008 Accessed online at: http://www.tannacomp.de/servicebereich/downloads/23626_MEDI_EVB_Handzettel.pdf.

Arranz, S et al. "Analysis of polyphenols in cereals may be improved performing acidic hydrolysis: A study in wheat flour and wheat bran and cereals of the diet," *Journal of Cereal Science*, May 2010.

Harbertson et al. "A guide to the Fining of Wine." *WSU Extension Manual EMO16.* Published Aug. 2009.

* cited by examiner

*Primary Examiner* — Nora M Rooney
(74) *Attorney, Agent, or Firm* — Norton Rose Fulbright US LLP

(57) ABSTRACT

The present invention relates to a composition for use in the treatment of an intestinal tract disorder caused by a gluten-associated protein, said composition comprising at least one agent which binds to the gluten-associated protein, characterized in that the composition is administered at the same time as or at most within 60 minutes after administration of at least one tannin to a patient.

17 Claims, No Drawings
Specification includes a Sequence Listing.

TANNIN AND ANTI-GLIADIN ANTIBODY COMPOSITIONS FOR TREATMENT OF A DISEASE OF THE INTESTINAL TRACT

CROSS REFERENCE TO RELATED APPLICATIONS

This application is a continuation of U.S. application Ser. No. 14/367,171, filed Jun. 19, 2014, now U.S. Pat. No. 9,724,326, which is a national phase application under 35 U.S.C. § 371 of International Application No. PCT/AT2012/050200 filed Dec. 19, 2012, which claims priority to Austrian Patent Application No. A 50010/2011, filed Dec. 19, 2011. The entire contents of each the above-referenced applications are incorporated herein by reference.

BACKGROUND OF THE INVENTION

1. Field of the Invention

The present invention relates to a composition for treating diseases of the intestinal tract which are caused by gluten and related substances.

2. Description of Related Art

Inflammatory processes in the intestinal tract may have various causes but in most cases they are difficult to diagnose and even more difficult to treat. In recent years, diagnosis of so-called food intolerances has become increasingly important in the professional medical world and thus has also yielded new findings for elucidating the causes of inflammatory processes in the intestinal tract.

Many people also develop an intolerance to histamine and other biogenic amines. In this case the efficiency of the diamine oxidase enzyme is not sufficient to effectively degrade the biogenic amines ingested with food. As a result, the excess histamine enters the bloodstream. Those affected typically develop headaches, diarrhea, unpleasant flatulence and other allergy-like symptoms after consuming certain foods.

The gluten intolerance, also known as celiac disease or sprue, is very complex. This disease is a complex combination of an absorption disorder and an interactive autoimmune reaction of the body, which to some extent also requires a genetic HLA predisposition, namely the HLA-DQ2 or DQ8 serotype. It is not yet understood why most of the population having this genetic predisposition develop a tolerance mechanism. Currently a number of definitions of disease syndromes which are triggered by gluten and/or gliadin can be found in the literature. These include, among others:

Asymptomatic celiac disease (also known as silent celiac disease): no symptoms either in the presence of gluten or in withdrawal; antibodies are present, and there is an increased risk of developing severe celiac disease.

Classical celiac disease: classical symptoms of malabsorption; diarrhea, steatorrhea, weight loss, failure to thrive. Usually diagnosed in children.

Subclinical celiac disease: tends to nonspecific symptoms such as iron deficiency, liver dysfunctions, some biopsy results may be available.

Symptomatic celiac disease: gastrointestinal/extraintestinal symptoms when gluten is consumed; broad spectrum of symptoms.

Refractory celiac disease (RCD): malabsorption and villous atrophy after more than 12 months of a strict gluten-free diet. The serology is usually negative; positive serology also indicates dietary mistakes.

Type I RCD: normal phenotype of the interepithelial lymphocytes.

Type II RCD: unchecked clonal expansion of interepithelial lymphocytes, precursor to enteropathy-associated lymphoma.

Latent celiac disease: positive serology with unremarkable histology of the small intestine or normal histology of the mucosa of the small intestine, which changes in response to administration of gluten or undiagnosed celiac disease or morphological deviations in the mucosa of the small intestine without any remarkable serology.

Potential celiac disease: positive serology, no villous atrophy.

Celiac disease autoimmunity: positive serology, characterized by elevated tTG ("tissue transglutaminase") or EMA ("endomysial components of antibodies") levels at a minimum of two measurement times.

Gluten intolerance: synonym for celiac disease or a nonspecific celiac-like disease that responds to a gluten-free diet.

Non-celiac gluten sensitivity (NCGS): general term for immunological, morphological or other symptoms that (may) occur in conjunction with ingestion of gluten. The innate immunity is activated but the serology is negative and there is no villous atrophy. This is a local gluten allergy with only local secretion of IgE.

Gluten-associated disorders: gluten ataxia, Duhring's disease (dermatitis herpetiformis).

A gluten allergy ("wheat allergy") is a completely different biochemically and physiologically. This is a classical IgE-mediated allergy to gluten, where sensitization of the lungs usually occurs through wheat flour dust.

The non-allergic immune response in celiac disease is triggered mainly by the alcohol-soluble protein fractions (so-called prolamines) of wheat (gliadin), rye (secalin), barley (hordein) and oats (avenin) as well as other fragments after peptic-tryptic digestion in the stomach.

These proteins as a group are referred to below as "gluten-related proteins." These proteins induce the immunological reaction spectrum of celiac disease in a manner that is reproducible in vitro and in vivo. They contain characteristic "amino acid repeats" consisting of proteins and glutamines. Examples that can be mentioned include the typical peptides: α-gliadin: LQLQPF(PQPLPY)$_3$PQPQPF; γ-gliadin: FLQPQQPF(PQQ)$_2$PY(PQQ)$_2$PFPQ; LMW-glutenin: QQQQPPFSQQQQSPFSQQQQ; HMW-glutenin: (GYYPTSPQQ)$_n$. The main trigger for the entire physiological celiac disease process is the passage of gluten that is only partially digested in the stomach through the epithelial cell layer of the small intestine into the lamina behind it.

SUMMARY OF THE INVENTION

The object of the present invention is to make available agents for preventing, reducing or ameliorating the inflammatory or immunological processes triggered by one or more gluten-related proteins in the intestinal tract.

The present invention therefore relates to a composition for use in treating a disease of the intestinal tract, which is triggered by a gluten-related protein, comprising at least one agent that binds to gluten-related protein, characterized in that the composition is administered to a patient simultaneously with or at most within 60 minutes (preferably 50 minutes, more preferably 40 minutes, even more preferably 30 minutes) after administration of at least one tannin.

According to the invention, this object is achieved by the combination of two means which are supplied orally in chronological sequence. The present invention presents for the first time a functional combination of two fundamentally different mechanisms of action. Firstly, the intestinal mucosa is stabilized with the help of tannins and absorption of potentially toxic substances is greatly reduced. At the same time or immediately thereafter, the toxic substances and/or mediators are bound by means of specific adductors and are thus removed from the physiological absorption process.

One object, namely the binding or masking of gluten-related proteins, is achieved according to the invention by means of specific antibodies, antibody fragments (e.g., light chains, antigen-specific binding sites and the like), aptamers, DARPINS or other suitable specific binding protein structures with which those skilled in the art are familiar. The production of these masking substances can be adapted to the respective prior art and optimized.

Antibodies or their fragments, which are secreted in egg yolk by laying hens following immunization with a desired antigen, are preferred. These immunoglobulins (IgY) have a structure resembling that of mammalian immunoglobulins IgG and IgE, but they do not interact with the mammalian immune system because of the absence of the FC domains.

Since the antibodies must be introduced into the intestine in a natural bioactive form, IgY from egg yolks is recommended preferentially because in this case an interaction with FC receptors of immune cells, rheumatoid factor and the complement system can be ruled out. This formation of specific IgY to gluten has already been performed (see US 2011/0008362, for example). As an alternative to IgYs, other polyclonal or monoclonal antibodies or their fragments may of course also be used if they can be modified according to the state of the art and made tolerable for humans. Additional antibodies in the sense of the invention can also be obtained from lizards or the blood of lungfish. Also preferred in the sense of the invention is the use of aptamers, which recognize specifically those epitopes that trigger or control adverse reactions in the gastrointestinal region. Those skilled in the art are familiar with the development and characterization of these aptamers.

The term "gluten-related proteins" as used here includes gliadin, secalin, hordein and avenin as well as their fragments after peptic-tryptic digestion in the stomach, but gliadin and its fragments are especially preferred. The following terms may therefore be used as synonyms for "gluten-related proteins": "gliadin, secalin, hordein and avenin and their fragments after peptic-tryptic digestion in the stomach," "gliadin, secalin, hordein and avenin and fragments produced therefrom by pepsin and/or trypsin" or "gliadin, secalin, hordein, avenin and fragments thereof." Fragments in the sense of the present invention consist of 5 to 100 amino acids, preferably 10 to 50 amino acids.

Tannins fulfill the task of stabilizing the intestinal mucosa. Tannins are a large family of related polyphenolic substances that occur in higher plants and algae. They are branched macromolecules according to the building block principle which share certain physicochemical properties: water solubility and the ability to attach themselves to proteins and to crosslink them, forming precipitates with alkaloids, and binding of chelate complexes with $Fe^{III}$ salts. According to the invention, various tannins, even in mixed form, may be used for stabilizing the mucous membranes. Tannins of the catechol tannin, Lamiaceae tannin or algal tannin type are preferred for use here. Sources of tannins include, for example: oak apples (Gallae); witch hazel leaves (Hamamelidis folium); walnut leaves (Juglandis folium); oak bark (Quercus cortex); ratanhia root (Raatanhiae radix); blood root (Tormentillae rhizome); blueberries (Myrtilli fructus); catechu; *Rubus fruticosus; Potentilla anserina; Fragaria vesca; Agrimonia eupatoria; Alchemilla xanthochlora; Plantago major; Plantago lanceolata, Rosa gallica; Sanguisorba officinalis* or also the seeds of dates, grapes, etc. Synthetic tannins may optionally also be used according to the invention, for example, polymers of acrylates, polyurethanes, isocyanates, derivatives of aldehydes but also the salts of minerals, for example, alums, chromium salts or zirconium salts may also be used.

According to one particularly preferred embodiment, the at least one tannin is selected from the group consisting of tannins, catechol tannins, Lamiaceae tannins and algal tannins.

The ability to crosslink proteins is based on a nonspecific addition of the phenolic structures to hydrophobic pockets as well as the development of hydrogen bridges between the hydroxyl groups of tannin and the side chains of amino acids. Addition of the tannins leads to folding and, in a sufficient concentration, crosslinking of the proteins.

Tannins are especially preferably used after being precipitated in advance with protein in a 20:80 ratio [tannin:protein], preferably 35:65, especially preferably 50:50 (for example, by bringing the tannin in contact with the protein/polypeptide). Proteins having a molecular weight between 50 kDa and 500 kDa in general may be used as the protein.

It has surprisingly been found that a double effect can be achieved by precipitating the tannin in advance with an antibody or binding protein: the resulting macromolecule combines the ability to crosslink the intestinal mucosa with the simultaneous ability to bind toxic antigens and substances and to reduce their bioavailability. The use of binding protein structures, which are precipitated with a tannin in advance in a ratio of 20:80 [tannin:protein], preferably 35:65, in particular preferably 50:50, is particularly preferred.

The present invention therefore relates to a composition comprising the combination of at least one tannin and at least one substance for binding or masking gluten-related proteins, so that the combination can be administered orally, with the goal of treating inflammatory or nonallergic immunological processes that are triggered by one or more gluten-related proteins in the intestinal tract.

In addition to the substance for binding or masking the gluten-related proteins and the tannin, bioactive microorganisms may also be administered to support the degradation of these toxic substances and/or mediators and thus suppress other potential pathological processes.

In another variant of the composition according to the invention, the specific bound toxic substances, peptides and/or antigens or mediators which also travel through the intestinal tract with the digested food mixture may also be degraded subsequently due to the administration of special bacterial proteases. In the case of celiac disease, the enzyme of choice is prolylendopeptidase (PEP; EC 3.4.21.26), which occurs in all living creatures. It is capable of degrading peptides that are formed from gluten and gliadin as the single enzyme to a certain extent. PEP occurs primarily as an intracellular enzyme; a few microorganisms, e.g., *Flavobacterium meningosepticum, A. niger*, as well as various Lactobacilli are also capable of secreting this enzyme. Additional microorganisms according to the invention include bacteria from the human oral cavity, for example, fusobacteria or actinomycetes.

The binding protein structures and tannins are preferably administered in a defined interval of time: firstly, the tannin preparation is administered orally in a period of time from 0 to 60 minutes, preferably 10 to 40 minutes, especially preferably 15 to 30 minutes before eating food that contains gluten.

According to one preferred embodiment of the present invention, the antibody, antibody fragment, aptamer and/or DARpin is directed against gliadin and/or fragments thereof, in particular against gliadin cleaved by tryptic and/or peptic action or physiologically equivalent metabolites of gluten or gluten fractions.

The at least one protein or polypeptide, in particular at least one antibody is preferably of a recombinant origin.

According to yet another preferred embodiment of the present invention, the at least one antibody is a polyclonal antibody from mammals, polyclonal antibody of avian origin, an antibody from lizards, a monoclonal antibody or an antibody from the blood of lungfish.

According to one preferred embodiment of the present invention, the composition according to the invention comprises eukaryotic and/or prokaryotic cells which are capable of reducing and/or suppressing inflammatory processes in the stomach and/or intestinal tract.

The cells present in the composition according to the invention are preferably capable of secreting proteins (such as enzymes, for example) that are capable of reducing and/or suppressing inflammatory processes in the intestinal tract, which are responsible for the development of an inflammatory disease.

According to one particularly preferred embodiment, the composition comprising at least one tannin is administered for treatment of an inflammatory disease of the intestinal tract in combination with at least one second agent for treatment of an inflammatory disease of the intestinal tract, wherein the at least one second agent induces or mediates at least one protein or polypeptide which binds at least one substance (actively) which induces or mediates the inflammatory disease and comprises eukaryotic cells and/or prokaryotic cells which are capable of reducing and/or suppressing inflammatory processes in the stomach and/or intestinal tract. In other words, the composition according to the invention, comprising at least one tannin, is administered in combination with a composition comprising at least one protein or polypeptide and a composition comprising eukaryotic cells and/or prokaryotic cells, both of which are defined above. The two compositions mentioned last may be supplied in either one or at least two individual dosages forms for administration.

According to one preferred embodiment of the present invention, the eukaryotic and/or prokaryotic cells are selected from the group consisting of *Flavobacterium* sp., *Lactobacillus* sp., *Aspergillus* sp. and *Bifidobacterium* sp.

The at least one tannin is preferably precipitated in advance with at least one protein.

According to another preferred embodiment of the present invention, the at least one agent, which binds to the gluten-related protein, and the at least one tannin are present in a formulation for controlled release in the stomach and/or intestinal tract, preferably the intestinal tract.

Those skilled in the art are familiar with agents for formulating active ingredients, which make it possible to provide a composition having the property of releasing, under certain conditions, the active ingredients incorporated into the composition. Such agents are used pharmaceutically to release active ingredients exclusively in the intestinal tract, for example. This has the advantage that the active ingredients can be passed through the stomach into the intestine by having an enteric coating that is resistant to gastric fluid.

The term "formulation for controlled release" comprises not only enteric dosage forms and/or formulations but also "delayed release" for release in the intestine with a time lag, sugar-degradable polymer coatings for release in the large intestine, coatings as a gel barrier for targeted release in the intestine depending on the thickness of the barrier, water-insoluble coatings with pore-forming agents which delay the release depending on the pore size and quantity, pH-sensitive coatings for release according to the physiological pH gradient, bioadherent coatings (chitosan, polyacrylates) that interact with the mucus and retain the dosage form, floating dosage forms for release in the stomach due to the fact that swelling occurs in the stomach and passage through the pylorus is prevented, processing in pellet form in a size of less than 1 to 3 mm for rapid passage of the active ingredients through the pylorus and transferred to the intestine.

It has proven particularly advantageous according to the invention that the tannins are administered before the composition according to the invention comprising the at least one agent that binds the gluten-related protein is administered before the composition according to the invention comprising the at least one agent because then the mucus membranes, in particular the intestinal mucus membranes are wetted with the tannins used according to the invention before the arrival of the aforementioned agents. This makes it possible first to stabilize the mucosa whereupon the actual active ingredients can be administered for treatment of the inflammatory disease.

The composition comprising at least one tannin is therefore administered at least one minute, preferably at least five minutes, more preferably at least ten minutes, most preferably at least 20 minutes before the at least one agent for treatment of an inflammatory disease of the intestinal tract.

According to one preferred embodiment of the present invention, the at least one tannin is administered in an amount of 10 mg to 10,000 mg, preferably 20 mg to 5000 mg, more preferably 50 mg to 2500 mg, especially preferably 100 mg to 2000 mg.

According to another preferred embodiment of the present invention, the at least one protein or polypeptide which binds to at least one substance (e.g., antigen) that induces or mediates the gluten intolerance is administered in an amount of 1 mg to 100,000 mg, preferably 5 mg to 50,000 mg, more preferably 10 mg to 20,000 mg, especially preferably 15 mg to 15,000 mg.

According to one particularly preferred embodiment of the present invention, the eukaryotic cells and/or prokaryotic cells are administered in an amount of $10^9$ to $10^{14}$, preferably $10^{10}$ to $10^{13}$.

The binding protein structures and tannins, which are used according to the invention, are administered according to the invention in a defined interval of time: first, the tannin preparation is administered orally within a period of 0-60 minutes, preferably 10-40 minutes, in particular preferably 15-30 minutes before eating the food that contains gluten.

When the compositions according to the invention are administered orally, they are formulated accordingly (for example, with an enteric coating that is resistant to gastric acid).

Yet another aspect of the present invention relates to a set for use in treatment of a disease of the intestinal tract, which is caused by a gluten-related protein, comprising at least one container that holds at least one tannin and at least one additional container that holds the composition according to the invention.

According to one preferred embodiment of the present invention, the set comprises compositions as defined above and is used for the purposes indicated above and in the manner described above.

ADDITIONAL EMBODIMENTS

1. A composition comprising at least one tannin for treatment of an inflammatory disease of the stomach and/or the intestinal tract, wherein the composition is administered in combination with at least one second agent for treatment of an inflammatory disease of the stomach and/or the intestinal tract.
2. The composition according to embodiment 1, characterized in that the inflammatory disease of the stomach and/or of the intestinal tract is selected from the group consisting of celiac disease, Crohn's disease, colitis, in particular cystic colitis, hemorrhagic colitis, ischemic colitis, pseudomembranous colitis or ulcerative colitis, irritable bowel and gastritis.
3. The composition according to embodiment 1 or 2, characterized in that the at least one second agent for treatment of an inflammatory disease of the stomach and/or of the intestinal tract comprises at least protein or polypeptide, which binds at least one substance that induces or mediates the inflammatory disease.
4. The compositions according to embodiment 3, characterized in that the at least one protein or polypeptide is an antibody, an aptamer and/or a DARpin ("designed ankyrin repeat protein") directed against a substance which induces or mediates the inflammatory reaction, or a specific receptor directed against an active ingredient that induces or mediates the inflammatory reaction.
5. The composition according to embodiment 4, characterized in that the at least one antibody, aptamer and/or DARpin is directed against gliadin and/or fragments thereof, in particular against tryptically and/or peptically cleaved gliadin or physiologically equivalent metabolites of gluten or gluten fractions.
6. The composition according to any one of embodiments 3 or 5, characterized in that the at least one protein or polypeptide, in particular the at least one antibody is of a recombinant origin.
7. The composition according to embodiment 4 or 5, characterized in that the at least one antibody is a polyclonal antibody from mammals, a polyclonal antibody of avian origin, an antibody from lizards, a monoclonal antibody or an antibody from the blood of lungfish.
8. The composition according to any one of embodiments 1 to 5, characterized in that the at least one agent for treatment of an inflammatory disease of the stomach and/or the intestinal tract comprises eukaryotic cells and/or prokaryotic cells, which are capable of reducing and/or suppressing inflammatory processes in the stomach and/or the intestinal tract.
9. The composition according to embodiment 8, characterized in that the eukaryotic and/or prokaryotic cells are selected from the group consisting of *Flavobacterium* sp., *Lactobacillus* sp., *Aspergillus* sp. and *Bifidobacterium* sp.
10. The composition according to any one of embodiments 1 to 9, characterized in that the at least one tannin is selected from the group consisting of tannins, catechol tannins, Lamiaceae tannins and algal tannins.
11. The composition according to any one of embodiments 1 to 8, characterized in that the at least one tannin is precipitated in advance with at least one protein.
12. The composition according to embodiment 11, characterized in that the at least one protein is an antibody defined as in one of embodiments 4 to 7.
13. The composition according to any one of embodiments 1 to 10, characterized in that the at least one tannin and the at least one agent for treatment of an inflammatory disease of the stomach and/or of the intestinal tract are present in a formulation for controlled release in the stomach and/or the intestinal tract, preferably the intestinal tract.
14. The composition according to any one of embodiments 1 to 13, characterized in that the composition comprising at least one tannin is administered simultaneously with and/or before the at least one agent for treatment of an inflammatory disease of the stomach and/or of the intestinal tract.
15. The composition according to any one of embodiments 1 to 14, characterized in that the composition comprising at least one tannin is administered at least one minute, preferably at least five minutes, more preferably at least ten minutes, most preferably at least 20 minutes before the at least one agent for treatment of an inflammatory disease of the stomach and/or of the intestinal tract.
16. The composition according to any one of embodiments 1 to 15, characterized in that the composition, comprising at least one tannin, is administered in an amount of 100 mg to 10,000 mg, preferably 100 mg to 5,000 mg, more preferably 100 mg to 2,500 mg, especially preferably 500 mg to 2,000 mg.
17. The composition according to any one of embodiments 3 to 7 and 10 to 16, characterized in that the at least one protein or polypeptide, which binds to the at least one substance that induces or mediates the inflammatory disease, is administered in an amount of 200 mg to 100,000 mg, preferably 200 mg to 50,000 mg, more preferably 200 mg to 20,000 mg, in particular preferably 500 mg to 15,000 mg.
18. The composition according to any one of embodiments 8 to 17, characterized in that the eukaryotic and/or prokaryotic cells are administered in an amount of $10^9$ to $10^{14}$, preferably $10^{10}$ to $10^{13}$,
19. A set for treatment of an inflammatory disease of the stomach and/or of the intestinal tract, comprising at least one container with at least one tannin and at least one additional container with at least one agent for treatment of an inflammatory disease of the stomach and/or of the intestinal tract.
20. The set according to embodiment 19, as defined in one of the embodiments 1 to 18.

The invention claimed is:

1. A composition suitable for a treatment of a disease of an intestinal tract of a subject, the composition comprising:
at least one tannin, wherein the at least one tannin is selected from a group consisting of gallotannins, catechol tannins, Lamiacea tannins, and algal tannins; and
at least one agent, wherein the at least one agent is an anti-gliadin antibody or a gliadin-binding fragment thereof.

2. A composition suitable for a treatment of a disease of an intestinal tract of a subject, the composition comprising:
at least one tannin, wherein the at least one tannin is selected from a group consisting of gallotannins, catechol tannins, Lamiacea tannins, and algal tannins; and
at least one agent, wherein the agent is an anti-gliadin antibody or a gliadin-binding fragment thereof, wherein the antibody is an immunoglobulin Y antibody.

3. The composition of claim 1, wherein the agent is a polyclonal antibody from a mammal, a polyclonal antibody from a bird, an antibody from a lizard, a monoclonal antibody, or an antibody from lungfish blood.

4. The composition of claim 1, wherein the disease of the intestinal tract is caused by a gluten-related protein.

5. The composition of claim 1, wherein the disease of the intestinal tract is a celiac disease.

6. The composition of claim 5, wherein the celiac disease is asymptomatic celiac disease, classical celiac disease, subclinical celiac disease, symptomatic celiac disease, refractory celiac disease, latent celiac disease, potential celiac disease, celiac disease autoimmunity, gluten intolerance, non-celiac gluten sensitivity, or a gluten-associated disorder.

7. The composition of claim 1, further comprising at least one bacterial protease, wherein the at least one bacterial protease is prolylendopeptidase.

8. The composition of claim 1, further comprising at least one eukaryotic and/or prokaryotic cell capable of reducing and/or suppressing inflammatory processes in a stomach and/or an intestinal tract, wherein the at least one cell is a cell of *Flavobacterium* sp., *Lactobacillus* sp., *Aspergillus* sp., or *Bifidobacterium* sp.

9. The composition of claim 8, wherein the composition comprises an amount of the at least one cell of $10^9$ to $10^{14}$ cells.

10. The composition of claim 9, wherein the composition comprises an amount of the at least one cell of $10^{10}$ to $10^{13}$ cells.

11. The composition of claim 1, wherein the composition is present in an oral dosage form.

12. The composition of claim 1, wherein the composition comprises 10 mg to 10,000 mg of the at least one tannin.

13. The composition of claim 12, wherein the composition comprises 50 mg to 2,500 mg of the at least one tannin.

14. The composition of claim 13, wherein the composition comprises 100 mg to 2,000 mg of the at least one tannin.

15. The composition of claim 1, wherein the composition comprises 1 mg to 15,000 mg of the at least one agent.

16. The composition of claim 15, wherein the composition comprises at least 5 mg of the at least one agent.

17. The composition of claim 16, wherein the composition comprises at least 10 mg of the at least one agent.

* * * * *

SEQUENCE LISTING

<160> NUMBER OF SEQ ID NOS: 4

<210> SEQ ID NO 1
<211> LENGTH: 30
<212> TYPE: PRT
<213> ORGANISM: Triticum spp

```
<400> SEQUENCE: 1

Leu Gln Leu Gln Pro Phe Pro Gln Pro Leu Pro Tyr Pro Gln Pro Leu
1               5                   10                  15

Pro Tyr Pro Gln Pro Leu Pro Tyr Pro Gln Pro Gln Pro Phe
            20                  25                  30

<210> SEQ ID NO 2
<211> LENGTH: 26
<212> TYPE: PRT
<213> ORGANISM: Triticum spp

<400> SEQUENCE: 2

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 3
<211> LENGTH: 20
<212> TYPE: PRT
<213> ORGANISM: Triticum spp

<400> SEQUENCE: 3

Gln Gln Gln Gln Pro Pro Phe Ser Gln Gln Gln Ser Pro Phe Ser
1               5                   10                  15

Gln Gln Gln Gln
            20

<210> SEQ ID NO 4
<211> LENGTH: 9
<212> TYPE: PRT
<213> ORGANISM: Triticum spp

<400> SEQUENCE: 4

Gly Tyr Tyr Pro Thr Ser Pro Gln Gln
1               5
```